(12) United States Patent
Myntti

(10) Patent No.: US 11,672,773 B2
(45) Date of Patent: Jun. 13, 2023

(54) METHODS FOR TREATING CILIATED CAVITIES

(71) Applicant: Next Science IP Holdings Pty Ltd, Chatswood (AU)

(72) Inventor: Matthew F. Myntti, Ponte Vedra Beach, FL (US)

(73) Assignee: Next Science IP Holdings Pty Ltd, Chatswood (AU)

( * ) Notice: Subject to any disclaimer, the term of this patent is extended or adjusted under 35 U.S.C. 154(b) by 10 days.

(21) Appl. No.: 17/549,227

(22) Filed: Dec. 13, 2021

(65) Prior Publication Data

US 2022/0184011 A1 Jun. 16, 2022

Related U.S. Application Data

(60) Provisional application No. 63/124,862, filed on Dec. 13, 2020.

(51) Int. Cl.
| | | |
|---|---|---|
| *A61K 31/194* | (2006.01) | |
| *A61K 47/10* | (2017.01) | |
| *A61K 9/00* | (2006.01) | |
| *A61P 31/04* | (2006.01) | |
| *A61K 47/20* | (2006.01) | |

(52) U.S. Cl.
CPC .......... *A61K 31/194* (2013.01); *A61K 9/0046* (2013.01); *A61K 47/10* (2013.01); *A61K 47/20* (2013.01); *A61P 31/04* (2018.01)

(58) Field of Classification Search
CPC .... A61K 31/194; A61K 9/0046; A61K 47/10; A61K 47/20; A61P 31/04
See application file for complete search history.

(56) References Cited

U.S. PATENT DOCUMENTS

| | | | | |
|---|---|---|---|---|
| 6,812,196 B2* | 11/2004 | Rees | ................. | C11D 3/2003 134/40 |
| 7,976,873 B2 | 7/2011 | Myntti et al. | | |
| 8,940,792 B2* | 1/2015 | Myntti | ................. | A01N 41/04 514/642 |
| 10,021,876 B2* | 7/2018 | Myntti | ................. | A01N 25/02 |
| 10,092,580 B2 | 10/2018 | Lighter et al. | | |
| 11,090,369 B2 | 8/2021 | Myntti | | |
| 11,219,208 B2* | 1/2022 | Myntti | ................. | A01N 25/02 |
| 11,234,435 B2* | 2/2022 | Myntti | ................. | A61K 8/463 |
| 2010/0209411 A1 | 8/2010 | Pellico | | |
| 2018/0369176 A1 | 12/2018 | Myntti | | |
| 2020/0315956 A1 | 10/2020 | Myntti | | |
| 2021/0368788 A1 | 12/2021 | Myntti | | |

FOREIGN PATENT DOCUMENTS

| | | |
|---|---|---|
| WO | WO-2022081737 A1 | 4/2022 |
| WO | WO-2022147055 A1 | 7/2022 |

OTHER PUBLICATIONS

Alexander G. Chiu, M.D. et al, "Baby shampoo nasal irrigations for the symptomatic post-functional endoscopic sinus surgery patient", American Journal of Rhinology, vol. 22, No. 1, Jan. 2008, pp. 34-37 (plus cover page).

Carolyn O. Diram, Ph.D. et al, "Ototoxicity of Next Science Middle Ear Wash™ in guinea pigs with otitis media", Department of Otolaryngology, University of Florida College of Medicine, Jul. 22, 2021, pp. 1-15.

Carolyn O. Dirain, PhD et al, "Ototoxicity of a novel antimicrobial solution in a guinea pig model", University of Florida, May 2020, 1 page.

* cited by examiner

*Primary Examiner* — Brandon J Fetterolf
*Assistant Examiner* — Manahil Mirghani Ali Abdalhameed
(74) *Attorney, Agent, or Firm* — Element IP, PLC; David G. Burleson

(57) ABSTRACT

A composition that can be used to treat a wide spectrum of gram positive and gram negative bacteria, including but not limited to those in biofilm form, can be used in cilia-containing areas such as the sinus cavities and middle/inner ear, while resulting in no, or very minimal amounts of, deciliation and/or loss of function (e.g., ability to clear material from the sinus cavity). Where such a targeted treatment area includes or might include a biofilm, the composition often can detach and assist in removing the biofilm from affected tissue.

17 Claims, 1 Drawing Sheet

METHODS FOR TREATING CILIATED CAVITIES

CROSS-REFERENCE TO RELATED APPLICATIONS

This application claims the benefit of U.S. patent appl. No. 63/124,862 filed on Dec. 13, 2020, the entirety of which is incorporated herein by reference.

BACKGROUND INFORMATION

Microbes are found virtually everywhere, often in high concentrations, and are responsible for a significant amount of disease and infection. Eliminating these microorganisms from targeted tissues is often desirable and sometimes critically important.

Bacteria present special challenges because they can exist in a number of forms, including planktonic, spore and biofilm, and their various self-preservation mechanisms make treating and/or eradicating them extremely difficult. (The term "treat" includes killing, inactivating and/or removal.) For example, the bacteria in biofilms or spores are down-regulated (sessile), making them resistant to attack by a large group of antibiotics and antimicrobials that are effective only during the active parts of a bacterium's lifecycle, e.g., cell division.

In a biofilm, microbes such as bacteria or fungi interact with and adhere to surfaces, forming colonies which facilitate continued growth. The microbes produce exopolysaccharide (EPS) and/or extracellularpolysaccharide (ECPS) macromolecules that keep them attached to a surface and form a protective barrier effective against many forms of attack. The small diameter of flow channels in the EPS/ECPS macromolecular matrix, which restricts the size of molecules that can reach the underlying microbes, and consumption of biocides through interactions with portions of the EPS/ECPS macromolecular matrix and microbe secretions and waste products contained therein probably play roles in the protective barrier function.

Due to the protection afforded by the macromolecular matrix and their down-regulated state, microbes in a biofilm state are very difficult to treat. The types of biocides and antimicrobials effective in treating microbes in this form often are strongly acidic or caustic, and often oxidizing due to the presence of halogen atoms, oxygen atoms, or both. Large dosages of such chemicals must be allowed to contact the biofilm for extended amounts of time to be effective, which makes them impractical for many applications.

Compositions intended for use in connection with compromised animal/human tissue which solvate a biofilm matrix so that it can be rinsed or otherwise removed from infected tissue have been described in, e.g., U.S. Pat. Nos. 7,976,873, 7,976,875, 7,993,675, and 7,959,943.

Compositions such as those described in the preceding paragraph, when applied to ciliated tissues such as exist in the sinus cavities and inner ear, can result in deciliation, i.e., the loss in functionality and/or removal of cilia, which are the relatively thick protruding organelles found in and projecting from the bed of eukaryotic cells. Sinus cavity cilia facilitate clearance of the sinuses, while those in the ear act as sound receptors.

Animal testing suggests that contributing factors in deciliation likely include the presence of ionic surfactants, high effective solute concentrations, and pH. Unfortunately, compositions described in the documents listed above all call for at least 0.2% (w/w) surfactant, some even much greater, and many require or prefer low pH and very high effective solute concentrations, i.e., osmolarities.

Because biofilms deciliate affected tissue anyway and because cilia in the sinus cavities can regrow within days, limited deciliation which does not impede clearing of the sinuses might be an acceptable side effect in a product intended for use in those sinus cavities not connected to the inner ear via a Eustachian tube. However, compositions intended for use in treating portions of the ear inward of the tympanic membrane (or treating a sinus cavity that is connected to the inner ear) cannot be permitted to result in deciliation because inner ear cilia do not regrow, resulting in irreparable hearing loss.

U.S. Pat. No. 11,090,369 describes compositions with a near-neutral pH which include at least 2% (w/v) non-aqueous liquid(s), a moderate amount of osmotically active solutes (e.g., no more 400 mOsm/L), at least 0.005% (w/v) of one or more enzymes which are active at the near-neutral pH, and 0 to 1% (w/v) anionic surfactant.

That which is desirable is an enzyme-free composition that can effectively treat microbes present in cilia-containing areas such as the sinus cavities and middle/inner ear, particularly microbes in a biofilm form, without resulting in unacceptable levels of deciliation. A composition that can accomplish the foregoing while also causing or facilitating detachment of biofilms from affected tissue is particularly desirable.

Also desirable are methods and techniques for rinsing a ciliated area susceptible to a bacterial infection, particularly a bacterial biofilm, at or about the time that the ciliated area has undergone an invasive procedure. Examples of such area are the middle ear during a myringotomy or tympanostomy procedure and a sinus cavity during a frontal endoscopic sinus surgery (FESS).

Further desirable is a composition that is sufficiently biocompatible so as to not require removal via irrigation with a saline rinse prior to being suctioned. Non-viscous liquids therefore are preferable.

SUMMARY

The present invention is directed to compositions that can be used to treat microbes including but not limited to bacteria, including those in biofilm form. The composition also can exhibit lethality toward other microbes such as viruses, fungi, molds, and yeasts.

Advantageously, this composition can effectively kill and/or wash away microbes present in areas having ciliated tissues such as the sinus cavities and middle/inner ear, even microbes in a biofilm form, while resulting in little to no deciliation in those areas. Where such a targeted treatment area includes a biofilm, the composition often can detach and assist in removing the biofilm from affected tissue.

The composition is free of enzymes and has a 4.8≤pH≤5.8. Its solvent component includes water and 2 to 20% (w/v) 95% purity ethanol, and its solute component includes sufficient amounts of anions from a weak acid plus both hydronium and metal cations so as to provide a buffered pH within the range set forth above as well as an effective solute concentration of from 100 to 300 mOsm/L. For a composition intended for introduction into the middle ear, no surfactant whatsoever is included. For a composition intended for introduction into the sinuses, up to ~1.5 g/L, preferably from 0.07 to 0.12% (w/v) anionic surfactant can be included.

The composition is provided as a liquid having physical properties, e.g., viscosity, similar to that of water. It also can be delivered via techniques employing a variety of presently available equipment.

All embodiments of the composition are biocompatible, while many embodiments are ciliacompatible.

The composition is effective at interrupting or breaking ionic crosslinks in the macromolecular matrix of a biofilm, which facilitates passage of the solutes and surfactant (if present) through the matrix to the microbes (e.g., bacteria) entrained therein and/or protected thereby. The composition thus bypasses and/or disables the biofilm defenses, allowing previously protected microbes to be accessed and killed, typically by processes that include inducing membrane leakage in bacteria, leading to cell lysis, or being washed away.

Embodiments of the composition can be used to treat chronic otitis media (i.e., with effusion or recurrent), cholesteatoma and other bacterial ear conditions, as well as chronic rhinosinusitis and other bacterial sinus conditions.

Often, a flowable form of the composition is introduced to an affected area peri- or intra-surgery. For example, a composition can be introduced into the middle ear via a myringotomy or a tympanostomy tube before or soon after insertion of the tube or, if deemed necessary or desirable, during a post-surgical follow-up evaluation. Advantageously, the composition need not be irrigated or otherwise rinsed out with a saline solution.

To assist in understanding the following description of various embodiments, certain definitions are provided immediately below. These are intended to apply throughout unless the surrounding text explicitly indicates a contrary intention:

"microbe" means any type of microorganism including, but not limited to, bacteria, viruses, fungi, viroids, prions, and the like;

"antimicrobial agent" means a substance having the ability to cause greater than a 90% (1 log) reduction in the number of one or more of microbes;

"active antimicrobial agent" means an antimicrobial agent that is effective only or primarily during the active parts of a microbe's lifecycle, e.g., cell division;

"biofilm" means a community of microbes, particularly bacteria and fungi, attached to a surface with the community members being contained in and/or protected by a self-generated macromolecular matrix;

"buffer" means a compound or mixture of compounds having an ability to maintain the pH of a solution to which it is added within relatively narrow limits;

"buffered" means containing the dissociation products of a buffer;

"buffer precursor" means a compound that, when added to a mixture containing an acid or a base, results in a buffer;

"polyacid" means a compound having at least two carboxyl groups and specifically includes dicarboxylic acids, tricarboxylic acids, etc.;

"solvate" means the process of taking a solid material into solution in a liquid;

"sequestering agent" means a chemical that assists in solvating a compound and in preventing the solvated form of that compound from coming out of solution;

"metal ion sequestering agent" means a sequestering agent that works in connection with one or more metal ions, particularly alkali and alkaline earth metals;

"soil load" means a solution of one or more organic and/or inorganic substances added to the suspension of a test organism to simulate the presence of body secretions, excretions, and the like;

"substituted," in reference to a functional group, means containing a heteroatom or functionality (e.g., hydrocarbyl group) that does not interfere with the intended purpose of the group in question;

"dwell time" means the amount of time that an antimicrobial agent is allowed to contact a bacterial biofilm;

"biocompatible" means presenting no significant, long-term deleterious effects on or in a mammalian species;

"ciliotoxic" means resulting in significant cleavage of or loss of function in cilia; and "ciliacompatible" means not significantly (e.g., <5%, <4%, or even <3%) ciliotoxic.

Hereinthroughout, pH values of a liquid are those which can be obtained from any of a variety of potentiometric techniques employing a properly calibrated electrode at room temperature (20° to 25° C.).

Any numerical limitation used herein includes an appropriate degree of uncertainty based on the number of significant places used with that particular numerical limitation. For example, "up to 5.0" can be read as setting a lower absolute ceiling than "up to 5."

DETAILED DESCRIPTION

Figure 1A:
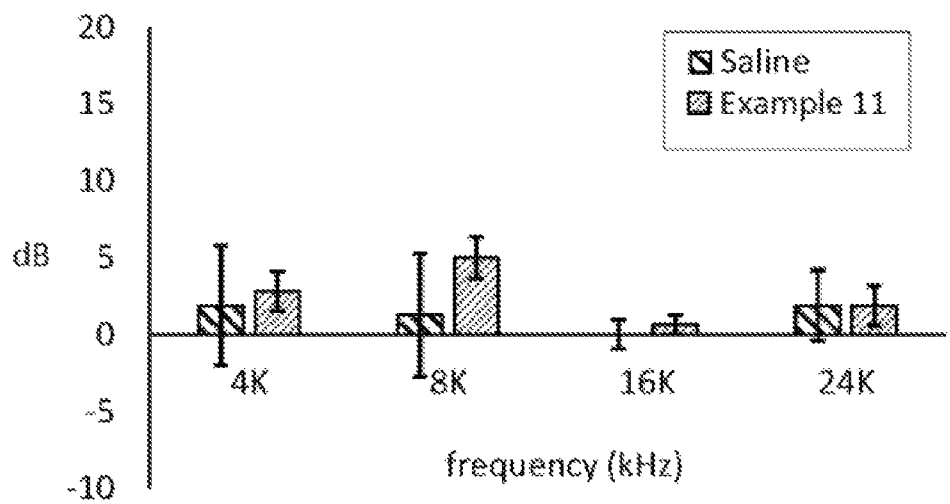
FIGS. 1A and 1B depict results of in vivo safety testing from Example 9.
Figure 1B:
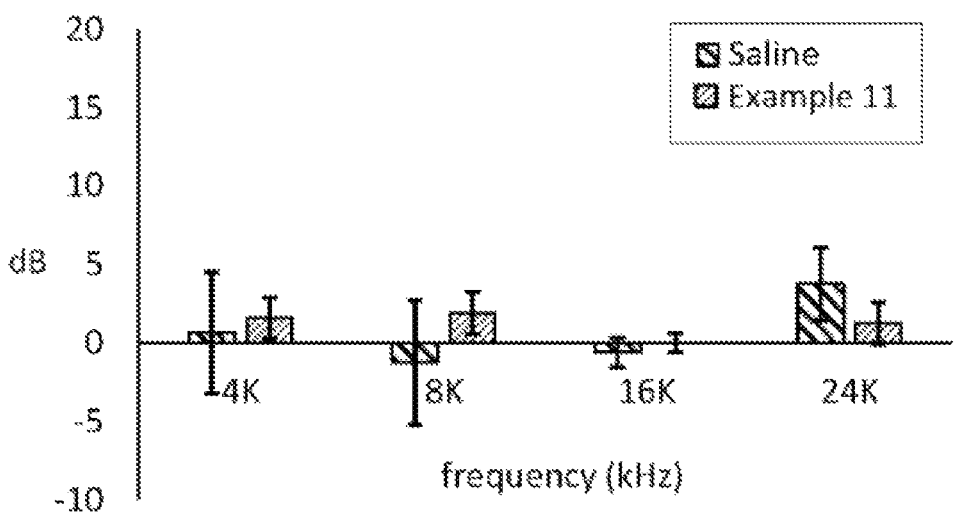

Compositions such as those summarily described in the preceding section can be used to break down, remove and/or disrupt biofilms including, advantageously, bacterial biofilms located in the middle or inner ear or the sinus cavities of an animal, particularly a mammal. The compositions are biocompatible and safe to use in and around the delicate tissues and structures of those areas because they are free of constituent materials which tend to harm such tissues and structures or unduly compromise long-term hearing.

The composition includes solvent and solute components.

The solvent component of the composition includes water and ethanol.

Water has a high solute holding capability, good wetting properties, excellent biocompatibility, environmental friendliness, and low cost. Essentially any source of water can be used, although those that are relatively free of bacteria without advance treatment are preferred. The water need not be distilled, deionized, or the like, although such treatments certainly are not excluded, particularly where the water employed might include undesirable solutes which might interfere with the intended purpose of the composition. To enhance solubility of one or more of the other components of the composition, the water can be heated.

Water has $\delta_p \approx 16.0$ MPa$^{1/2}$, where $\delta_p$ is the dipolar intermolecular force (polarity) Hansen Solubility Parameter (HSP), a common method for predicting whether one material will dissolve in another to form a solution.

Each component in a mixture or composition has three HSPs: dispersion, dipole-dipole (polarity) interactions, and hydrogen bonding. These parameters are generally treated as coordinates in three dimensions, with HSP characterizations being visualized using a spherical representation: the 3D coordinates are at the center of the sphere with the radius of the sphere ($R_0$ or "interaction radius") indicating the maximum difference in affinity tolerable for a "good" interaction with a solvent or solute. In other words, acceptable solvents lie within the interaction radius, while unacceptable ones lie outside it.

The distance between the HSPs of two materials in so-called Hansen space ($R_a$) can be calculated according to the following formula:

$$(R_a)^2 = 4(\delta_{d2}-\delta_{d1})^2 + (\delta_{p2}-\delta_{p1})^2 + (\delta_{h2}-\delta_{h1})^2 \quad (I)$$

where $\delta_d$ is the energy from dispersion forces between the molecules, $\delta_p$ is the energy from dipole-dipole intermolecular forces, and $\delta_h$ is the energy from hydrogen bonds between molecules.

A simple composite affinity parameter, the Relative Energy Difference (RED), represents the ratio of the calculated HSP difference ($R_a$) to the interaction radius ($R_0$), i.e., RED=$R_a$/$R_0$. In situations where RED<1.0, the solubilities of the molecules are sufficiently similar that one will dissolve in the other. In situations where RED>1.0, the solubilities of the molecules are not sufficiently similar for one to dissolve the other. In situations where RED≈1.0, partial dissolution is possible.

The dipole-dipole interaction Hansen solubility parameter for a particular solution or mixture of solvents can be calculated according to the following formula:

$$\delta_p = \sum_{i=1}^{n} (\delta_{di} \times x_{di}) \quad (II)$$

where $\delta_{di}$ is the energy from dipolar intermolecular force for solvent i, $x_{di}$ is the percentage of solvent i in the solvent portion of the composition, and n is the total number of solvent components.

Hereinthroughout, the $\delta_p$ value for a given liquid is determined at room temperature; because solubility typically increases with increasing temperature, meaning that the dissolution rate of the macromolecular matrix and the bacterial cell wall proteins increase with increasing temperatures, the efficacy of the inventive composition is expected to increase at higher temperatures.

More details about HSPs and related concepts can be found in, for example, U.S. Pat. No. 10,021,876.

In the present compositions, the overall $\delta_p$ of the solvent component is below that of water. More specifically, the overall $\delta_p$ of the solvent component is generally from 14.5 to 15.9 MPa$^{1/2}$, preferably from 14.7 to 15.8 MPa$^{1/2}$, more preferably from 14.9 to 15.7 MPa$^{1/2}$, and most preferably 15.5±0.2 MPa$^{1/2}$.

The foregoing reduction in the overall $\delta_p$ of the solvent component is achieved by including from 2 to ~20%, preferably from 2.5 to 15%, more preferably from 3 to 12.5%, even more preferably from 3.5 to 10%, and most preferably from 4 to 7% (all w/v) ethanol. (Because of the sensitive nature of cilia, absolute (anhydrous) ethanol is contraindicated because of the chemicals needed to remove residual water, so the amounts of ethanol here refer to so-called 190 proof ethanol, which is provided at ~95% purity, with some variance depending on the supplier. Thus, although 200 g of 190 proof ethanol in a 1 L solution (20% (w/v)) yields roughly 19 g of ethanol molecules, this nevertheless is referred to herein as 20% (w/v) ethanol.)

The U.S. Food and Drug Administration (FDA) considers ethanol to be an inactive ingredient for topical applications at levels up to 25%, which is above the maximum amount set forth the preceding paragraph. Nevertheless, for compositions intended for introduction into the middle ear, where ciliotoxicity is of greatest concern, the amount of ethanol preferably is kept below 8%, more preferably below 7%, and most preferably below 5.5% (all w/v).

In addition to the solvent component, the composition also includes as a primary component a solute component which includes buffered dissociation products of citric acid. This can be achieved by dissolving both citric acid and a (separately provided) salt thereof in the solvent component or by reacting some solvated citric acid with a less-than-stoichiometric amount of strong base such as an alkali metal hydroxide, e.g., NaOH. In both cases, the result is citrate anions, hydronium ions, and cations other than hydronium ions, e.g., Na$^+$ ions.

Citric acid is available in hydrated and anhydrous forms, with either being capable of being used.

Widely available salts of citric acid include trisodium citrate (typically available as a dihydrate), tripotassium citrate (typically available as a monohydrate), disodium hydrogen citrate, dipotassium hydrogen citrate, sodium dihydrogen citrate, and potassium dihydrogen citrate. Other salts are commercially available, albeit not as widely.

The amounts of each of the sub-components are constrained by both the desired pH and the desired overall solute concentration.

Each of U.S. Pat. Nos. 8,940,792, 9,314,017, 9,872,843, 10,021,876, 10,477,860, 10,780,037, 10,827,750, 11,118,143 and similar suggests that a decrease in pH generally corresponds with enhanced efficacy. However, because the present composition is desired to be biocompatible and have minimal (little-to-no) ciliotoxicity, the targeted pH range above has the effect of negating, or at least severely mitigating, a key efficacy-enhancing variable from those prior teachings. The present compositions are intended to have 4.8≤pH≤5.8, preferably 4.9≤pH≤5.7, and more preferably 5.0≤pH≤5.6; a preferred composition has a pH of 5.25±0.3.

Each of the foregoing pH values is substantially higher than that of even a relatively dilute aqueous solution of citric acid. Thus, in some embodiments, the dissociation products of separately provided salt(s) of citric acid is/are included while, in other embodiments, the foregoing pH values are obtained by adding a strong base to solvated citric acid to form a buffered solution. In both cases, the result is a buffered solution based on dissociation products of citric acid.

Additionally, the overall effective solute concentration of the composition ranges from 100 to 300, preferably from 100 to 280, and more preferably 215±60 mOsm/L. Embodiments of the composition can exhibit minimum solute concentrations of 105, 110, 115, 120, 125, 130, 135, 140, 145, 150, 155, 160, 165, 170, 175 or 180 mOsm/L and maximum solute concentrations of 275, 260, 250, 245, 240, 235, 230, 225, 220, 215, 210, 205, 200, 195, 190 or 185 mOsm/L. Ranges based on each of the minimums and each of the maximums are envisioned, with some exemplary options including, but not being limited to, 110 to 275, 125 to 250, 150 to 250, 160 to 240, 160 to 225, 175 to 250, 170 to 240, 170 to 230, 180 to 240, 180 to 235, and 180 to 220 mOsm/L.

Effective solute concentration can be fairly closely approximated by calculation or, if desired, can be determined by testing. For example, from a properly calibrated DSC unit-produced scan acquired over a temperature range that includes the melting temperature of a given liquid composition, one can determine effective solute concentration from latent heat of fusion calculations. Alternatively, thermogravimetric analysis can provide a good indication of the amount of solutes in a composition.

A preferred method of determining effective solute concentration is through a colligative property such as freezing point depression. Such units typically measure osmolality rather than osmolarity, but knowing or calculating the density of a composition permits its osmolarity to be determined.

One adaptation that must be made is to account for the effect of ethanol (which itself impacts freezing point), which is done by replacing with water the volume of ethanol in the solution being analyzed. For example, if the recipe for a given composition is to add 4.9 g citric acid and 13.1 g trisodium citrate to a container followed by 50 g ethanol (190 proof) before adding sufficient water to yield 1 L, the solution to be subjected to the freezing point depression test has its ethanol replaced by water. Because osmolarity is a colligative property and because the behaviors of citric acid and citrates in a water-ethanol mix are substantially similar to their behaviors in pure water, the effective solute concentration value determined from the freezing point depression test (performed on the water-only solution) can be deemed to be a good approximation of the actual value of the original composition (ethanol-water blend).

Taking into account the foregoing pH and effective solute concentration constraints, and using anhydrous citric acid and trisodium citrate dihydrate as exemplary versions of the acid and salt, the resulting per-liter masses of each generally range from 4.6 to 5.0 g of the former and from 12.5 to 13.5 g of the latter. Ordinarily skilled artisans are able to adapt the foregoing to account for different forms of the acid and salt, as well as to swap out the salt for an increased amount of acid and a strong base (or basic solution) to achieve a substantially equivalent target pH and effective solute concentration. (Reference also can be made to texts, articles, online calculation tools, etc., to determine how much of a given strong base, usually in aqueous form, to add to a solution containing a given amount of citric acid.)

In those embodiments where the solute component is provided by separately adding the acid and one or more separately provided salts thereof, if the amount of total citrates necessary to achieve the desired effective solute concentration will result in the pH being above the permitted upper limit, one or more inactive ionic compounds, particularly electrolytes (e.g., NaCl, KCl, etc.; see, e.g., U.S. Pat. No. 7,090,882), can replace some of the citric acid and/or citrate, thereby increasing the effective solute concentration until the value falls within the desired range. Essentially any compound that at least partially dissociates in water and/or the organic liquid(s) employed in the solvent component can be used to achieve this effect, with exemplary compounds including, but not being limited to, phosphates, acetates and any material deemed to be an "inactive ingredient" in injections, gels, creams, lotions, and/or ointments by governmental regulatory bodies.

Alternatively, if the amount of citric acid and citrate salt(s) results in an acceptable effective solute concentration but a pH that is above the permitted upper limit, the overall composition can be titrated with a small amount of concentrated acid (e.g., 37% HCl) until the desired pH is reached. (The same can be done with a concentrated caustic solution if the pH of a given composition turns out to be below the permitted pH lower limit.)

Each of the foregoing solute component subcomponents generally is considered to be both biocompatible and ciliacompatible.

In embodiments not intended for introduction into the ear, a small amount of one or more anionic surfactants also can be included in the solute component.

Potentially useful anionic surfactants include, but are not limited to, sodium chenodeoxycholate, N-lauroylsarcosine sodium salt, lithium dodecyl sulfate, 1-octanesulfonic acid sodium salt, sodium cholate hydrate, sodium deoxycholate, sodium glycodeoxycholate, sodium lauryl sulfate (SLS), and the alkyl phosphates set forth in U.S. Pat. No. 6,610,314. SLS constitutes a preferred anionic surfactant.

Each of the documents set forth above in connection with the discussion on pH requires moderate-to-high levels of one or more surfactants. Because the compositions of the present invention are intended to be used in the presence of cilia and because many types of surfactant are known to be ciliotoxic, inclusion of such levels of surfactant(s) is contraindicated. Again, this means that an efficacy-enhancing option from the aforementioned prior teachings is not available (or much less available) in compositions of the present invention.

For embodiments of the composition intended for otic applications, no surfactants whatsoever are included, while very limited amounts can be included in embodiments intended for sinus applications. The amount of anionic surfactant to be included in the latter embodiments is no more than 0.15%, commonly less than 0.14%, typically less than 0.13%, preferably less than 0.125%, and more preferably less than 0.12%, all in w/v format. A generally preferable range of anionic surfactant concentration for non-otic applications is 1.05±0.1 g/L.

The solute component thus provides to the composition a slightly acidic pH and a moderate amount of osmotically active solutes, often having an effective solute concentration of no more than 250 mOsm/L and commonly no more than 235 mOsm/L. Some embodiments include no more than 0.025% (w/v) of one or more anionic surfactants, while others include no added surfactant.

Embodiments of the composition have a sufficiently low viscosity to enable delivery using techniques such as lavage, misting, wicking and dripping, although the preferred methods are streams and sprays. These and other embodiments of the composition also can be easily removed from the treatment site by subsequent draining or, more commonly suction; saline irrigation is unnecessary. Many embodiments are sufficiently biocompatible and ciliacompatible to permit non-removed quantities to be absorbed.

While not wishing to be bound by theory, citrate ions are believed to act as metal ion sequestering agent, complexing or otherwise reacting with metal ions in a biofilm. When those metal ions, which act to crosslink, bridge or otherwise assist in binding together polymer chains in the EPS/ECPS matrix of a biofilm, other components of the composition can more effectively act on the polymer chains and/or the bacteria under and/or within the EPS/ECPS matrix. Unbound (non-crosslinked) polymer chains or fragments can be solvated, breaking down the matrix, permitting its component parts to be brought into solution or suspension so that they can be flushed or otherwise removed from the treatment area. Remnants of the biofilm might be able to be removed along with the composition via suction.

Various embodiments of the present invention have been provided by way of example and not limitation. General preferences regarding features, ranges, numerical limitations and embodiments are, to the extent feasible, as long as not interfering or incompatible, envisioned as being capable of being combined with other such generally preferred features, ranges, numerical limitations and embodiments.

The composition can be prepared in a number of ways. Description of an exemplary method follows.

Each of the solute subcomponents can be added to sufficient water to constitute 60-90% of the calculated desired volume. This solution can be stirred and/or heated if desired. The desired weight of 190 proof ethanol then can be added. Once stirring, if used, is complete, sufficient water is added so as to bring the composition to the calculated osmolarity and pH value. Advantageously, no special conditions or containers are needed to store the composition for an extended time, although refrigeration can be used if desired.

The composition conveniently can be provided as a solution and then used as-is in the techniques described below.

An advantage of the composition described herein is an ability to detach biofilms from the tissues to which they are attached. Regardless of whether this occurs, the composition can significantly reduce the number of viable bacteria remaining on or around the affected tissue.

After such initial reductions, compositions described herein also can inhibit regrowth of biofilms. Examples of this are shown below in the Examples section.

The composition can act at least in part to interrupt or break ionic crosslinks in the macromolecular matrix of a biofilm, facilitating passage of solutes and surfactant (if present) through the matrix to bacteria entrained therein and/or protected thereby. Disruption of the macromolecular matrix advantageously also can result in detachment of the biofilm, alternatively or in addition to treating bacteria entrained in that matrix.

Ciliotoxicity generally increases with increasing surfactant concentration, increasing tonicity, and/or departure of pH from neutral. Given the foregoing description, the ordinarily skilled artisan can provide a ciliacompatible composition that remains effective against microbes in biofilm form.

An otic composition can be delivered to the targeted areas of the ear during and/or after a surgical procedure such as, but not necessarily limited to, a myringotomy performed as part of insertion of a vent tube.

Before the tympanic membrane is incised, its outer surface can be washed or rinsed. At this point, where the composition is not expected to pass the tympanic membrane and can be rinsed or lavaged, a composition having a lower pH (pH≈4) and/or higher effective solute concentration (e.g., 400 to 700 mOsm/L) can be employed. Where an analgesic such as phenol is to be applied prior to incision, this would be performed prior to application of the analgesic.

Once the tympanic membrane has been incised, the present composition can be delivered to the middle/inner ear through a tympanostomy tube or via syringe inserted through the tympanic membrane incision. In both cases, a medical professional can continue to insert composition until liquid backflow is observed. (A typical human middle ear holds 1 to 1.5 mL of liquid, by way of example.) In some embodiments, this optionally can be followed by suctioning and, still further, optionally by repeating one or both of the foregoing steps.

For sinus applications, the composition can be introduced to the sinus cavity via a surgical technique such as trephination or via a remote delivery mechanism such as, e.g., a Hydrodebrider™ endoscopic sinus irrigation system (Medtronic; Minneapolis, Minn.) or a Relieva Vortex™ sinus irrigation catheter (Acclarent, Inc.; Irvine, Calif.). Regardless of delivery mechanism, a medical profession can continue delivering composition to the targeted cavity(ies) until returning effluent appears visually clear.

Regardless of where used, the composition can be permitted a dwell time of a few seconds up to several hours. Targeted dwell time typically depends on the nature of the patient (e.g., ability to be sufficiently immobile to permit a long dwell time) as well as the physiology of the area to be treated, e.g., whether liquid introduced to that area naturally drains or pools.

As mentioned previously, flushing or rinsing of the treated area typically is not necessary, although irrigation with a liquid such as a normal saline solution certainly can be done if desired.

Although sterilized, medical device implants such as tympanostomy tubes can become colonized, prior to and during implantation, with bacteria from the environment, from a healthcare worker, or more commonly from bacteria present on the patient's own skin. After insertion, these implants can become colonized from systemic bacteria which make their way to the implant which provides a surface for biofilm growth because the implant surface is not protected by the host immune defenses. In addition, currently employed sterilization techniques are not designed to remove EPS/ECPS, the presence of which greatly facilitates formation of a biofilm; therefore, even a sterilized device/article that is properly implanted can have EPS/ECPS on its surface from previous exposure.

If a biofilm forms on an implant, no currently available treatment can eradicate it. Systemic antibiotics are ineffective against such infections, certainly due to the inherent protection by the EPS/ECPS but also perhaps due to limited blood supply at the surface of the implanted article.

Another envisioned usage of the present compositions is in preparation for and during introduction of cochlear implants, as well as in post-implementation disinfection of such implants. The antimicrobial compositions can be effective topical treatments, applied to a to-be-implanted device or article or can be used to wash an infected implant and surrounding tissue to rid the body of a biofilm and/or biofilm-forming materials such as EPS/ECPS.

The tympanic membrane where the implant is or was located likewise can be treated with the previously described composition. This can be done at the time of the original implantation (i.e., immediately following insertion of the article), and can be followed with rinsing/irrigation, suctioning or both.

As has been mentioned several places above, deciliation is a significant concern for any composition that is intended for use in the sinus cavities and, particularly, the middle-inner ear. While deciliation is preferably avoided altogether, no more than ~20%, preferably no more than ~15%, and more preferably no more than ~10%, is acceptable for compositions intended for use in sinus applications. For otic compositions, the acceptable upper limit is that which results in measurable hearing loss. Deciliation can be determined via scanning electron microscopy, as described more fully below, and/or audiometric testing.

The relevant portions of any specifically referenced patent and/or published patent application are incorporated herein by reference.

EXAMPLES

Examples 1-8: Safety Screening

Eight compositions were prepared for purposes of evaluating potential ciliotoxicity. Their components (in grams) and properties are tabulated below, all based on a total volume of 1 L. The ethanol was 190 proof, the citric acid (CA) was anhydrous, and the trisodium citrate (TSC) was in dihydrate form. Effective solute concentration (osmolarity) values are calculated, rounded to the nearest 10. (The final pH was achieved by titrating with a strong acid or base solution, as needed.)

TABLE 1

Components and properties

| | 1 | 2 | 3 | 4 | 5 | 6 | 7 | 8 |
|---|---|---|---|---|---|---|---|---|
| ethanol | 50.0 | 50.0 | 50.0 | 50.0 | 100.0 | 100.0 | 150.0 | 100.0 |
| CA | 5.94 | 5.94 | 4.50 | 4.50 | 57.94 | 8.25 | 38.63 | 5.50 |
| TSC | 13.00 | 13.00 | 15.00 | 15.00 | 55.37 | 114.50 | 36.91 | 76.33 |
| SLS | 0.0 | 1.0 | 0.0 | 1.0 | 5.0 | 5.0 | 0.0 | 0.0 |
| pH | 5.0 | 5.0 | 5.5 | 5.5 | 4.0 | 6.0 | 4.0 | 6.0 |
| osmolarity (mOsm/L) | 220 | 230 | 230 | 240 | 1290 | 1500 | 860 | 1000 |
| $\delta_p$ (MPa$^{1/2}$) | 15.64 | 15.64 | 15.64 | 15.64 | 15.28 | 15.28 | 14.92 | 15.28 |

To evaluate the safety of these formulations when used in the middle ear, cilia beat frequency (CBF) testing was used as a screening method. CBF testing was performed as follows.

Images were visualized using a 63× objective on a Leica DM IL inverted microscope (Leica Microsystems, Inc., Bannockburn, Ill.). Experiments were performed at 27.5° to 28.5° C. Once a stable baseline was obtained, 20 µL of test solution was gently pipetted onto the apical surface of the culture. Images were captured using a Model A602f-2 Basler area scan high-speed monochromatic digital video camera (Basler AG; Ahrensburg, Germany) at a sampling rate of 100 frames per second with a resolution of 640×480 pixels. The video images were analyzed using the Sisson-Ammons Video Analysis (SAVA) system version 2.1.12. For each experiment, beating cilia on the edge of the tissue culture specimen were detected. The digital image signal was then routed from the camera directly into a digital image acquisition board (National Instruments) within a desktop PC. Images were captured, compressed, and stored to disk. Files were then reloaded and analyzed with virtual instrumentation software highly customized to perform ciliary beat frequency (CBF) analysis.

Beating cilia were observed and recorded every 30 seconds for CBF determination. Once a stable baseline was obtained (~3 minutes), 20 µL of test solution was gently pipetted onto the apical surface of the culture. Recordings continued for ~15 minutes. Each experimental condition was repeated in cultures from at least 3 subjects.

The mouse nasal septum was harvested (as described in M. B. Antunes et al. "Murine Nasal Septa for Respiratory Epithelial Air-liquid Interface Cultures," *Biotechniques* 2007; 43:195-204) and placed in sterile phosphate buffered saline. All experiments were run between 27.5° to 28.5° C.

Septal explants were placed in a glass perfusion chamber held in place with a nylon grid (1.5 mm) whose outer frame snapped into the inside of the perfusion chamber (PH1 Warner Instruments; Hamden, Conn.). Beating cilia were identified along the edges of the explant using a Leica DMLFSA microscope set on an air table (TMC; Peabody, Mass.) using a water immersion 63× objective and differential interference contrast (DIC) optics (Leica Microsystems, Inc.). Once beating cilia were observed, 2-second videos were captured using the aforedescribed Model A602f-2 Basler camera at a sampling rate of 100 frames per second with a resolution of 640×480 pixels. The video images were analyzed using the SAVA system described above. All-digital image capture and whole-field analysis of ciliary beating frequency was per *J. Microsc.* 2003; 211: 103-111. For each experiment, beating cilia on the edge of the tissue culture specimen were detected. Digital image signals were routed, processed and analyzed as described above.

Once a ciliary beat frequency was established, the test solution or control solution was applied to the chamber and 2-second video recordings were performed every minute for the ensuing 30 minutes. Each solution was tested a minimum of three times.

In this testing, a composition which maintains the same number of beating cilia as an untreated comparative is considered to be "safe" (because cilia have not been removed or deactivated by exposure). Tabulated below are the percentages of cilia which retained activity after 15 minutes of exposure for each of the compositions summarized above in Table 1.

TABLE 2

Remaining cilia (%)

| 1 | 2 | 3 | 4 | 5 | 6 | 7 | 8 |
|---|---|---|---|---|---|---|---|
| 80 | 66 | 94 | 96 | 0 | 0 | 23 | 69 |

The results from Table 2 were plotted against the amount of each of SLS, pH, $\delta_p$ and osmolarity to provide guidance for product development and further testing.

Example 9: In Vivo Safety Testing, Middle Ear

A composition similar to that used in Examples 1-8 above was employed in testing on live guinea pigs. Its components and properties are tabulated below. (All abbreviations and explanations set forth above in Examples 1-8 apply here as well.)

TABLE 3

Components and properties

| | 9 |
|---|---|
| water | 929.00 |
| ethanol | 50.00 |
| CA | 4.81 |
| TSC | 13.00 |
| pH | 5.0 |
| osmolarity (mOsm/L) | 210 |
| $\delta_p$ (MPa$^{1/2}$) | 15.64 |

After an acclimation period of 5-7 days, the test animals were subjected to baseline hearing tests.

Thereafter, using a 27-gauge blunt-tipped needle, each of 8 test animals received the composition from Table 3 in one middle ear space and saline (control) in the other. (The mean middle ear volume of these test subjects was ~0.2 mL.) Otomicroscopy was performed after each of the foregoing steps.

Each test animal was assessed daily, including an observation of the tympanic membranes, signs of ataxia, and any head tilting. (Guinea pigs tend to tilt their heads downward in the direction of an ear which is painful.)

After one week and after 8 weeks, hearing tests were conducted at volumes of 0 to 100 dB in 5 dB steps and four frequencies (4 kHz, 8 kHz, 16 kHz and 24 kHz). Otomicroscopy again was performed after each hearing test.

The results of the hearing tests are summarized in FIGS. 1A (1-week threshold shift) and 1B (8-week threshold shift), where a negative value indicates a mean post-injection hearing threshold better than a corresponding mean baseline threshold. The results strongly suggest (p>0.05) that hearing thresholds between ears receiving the test composition and those receiving the control saline solution did not differ at both 1 week and 8 weeks after onset of treatment.

After the last hearing test and euthanization, the pathology of each test animal's middle ear and cochlea was determined. Any pathology that might have been observed during the evaluation was resolved by this point (i.e., none was observed), but half of the guinea pigs receiving the tested composition had dark spots in the bulla.

SEM microscopy showed no differences in outer hair cell loss in the cochlea of the two groups of test animals. Thus, a single dose exposure of a middle ear to an inventive composition caused transient inflammation but no evidence of inner ear toxicity including, but not limited to, ciliotoxicity.

Examples 10-11: Planktonic Bacteria Testing

The tests described below were performed using the two compositions tabulated below. (All abbreviations and explanations set forth above in Examples 1-8 apply here as well.)

TABLE 4

| Components and properties | | |
|---|---|---|
|  | 10 | 11 |
| ethanol | 50.0 | 50.0 |
| CA | 5.9 | 5.9 |
| TSC | 13.0 | 13.0 |
| SLS | 0.0 | 1.0 |
| pH | 5.0 | 5.0 |
| osmolarity (mOsm/L) | 220 | 220 |
| $\delta_p$ (MPa$^{1/2}$) | 15.64 | 15.64 |

The procedure of ASTM E2315-16 was used to evaluate suspension time kill (STK) at 60 seconds dwell time.

The M07 (11th ed., January 2018) procedure of the Clinical and Laboratory Standards Institute ("Methods for Dilution Antimicrobial Susceptibility Tests for Bacteria That Grow Aerobically") was used to determine minimum inhibitory concentration (MIC) and minimum bactericidal concentration (MBC).

Each of the foregoing was performed on both *S. aureus* and *P. aeruginosa* (presented as SA and PA, respectively, below.) The following table presents STK results in terms of log reduction and MIC and MBC as percentage reductions.

TABLE 5

| | Planktonic tests | | | |
|---|---|---|---|---|
| | 10 | | 11 | |
| | SA | PA | SA | PA |
| STK | 0.4 | 0.2 | 6.1 | 0.2 |
| MIC | 12.5 | 50.0 | 12.5 | 50.0 |
| MBC | 12.5 | 50.0 | 12.5 | 50.0 |

Examples 12-13: Biofilm Testing

The two compositions from Examples 10-11 also were tested on biofilms of the same two types of bacteria employed in the planktonic testing. Normal saline was used as a control for each.

The particular test employed here involved application of a composition to a preformed biofilm for 60 minutes, then measuring the amount of biofilm regrowth over time. The specifics of this procedure were as follows.

Preparation of Microorganisms

Isolated colonies were aseptically removed from the surface of tryptic soy agar plates from recently grown stock culture, and mixed into tubes with 10 mL of 30% tryptic soy broth supplemented with 2.5 g/L of glucose. The tubes were incubated overnight on an orbital shaker at 160 rpm and 37° C. The overnight cultures were diluted 1:100 into fresh 30% tryptic soy broth supplemented with 2.5 g/L of glucose. This was the working culture for the test procedure.

Test Procedure

1. Growth of Biofilm
   a. 96-well microtiter plates (86×128 mm) were designated with 8 rows A-H and 12 columns 1-12. 200 µL of sterile distilled water was added to each of the 8 wells in column 1. 200 µL of sterile 30% tryptic soy broth supplemented with 2.5 g/L glucose was added to wells 2-12 of row A. 200 µL of bacterial working culture was added to each of the remaining 77 wells (wells 2-12 of rows B-H).
   b. Bacterial Growth
      i. A BreatheEasy™ sealing membrane was placed on the microtiter plate, and the plate was incubated at 36° C. for 24 hours.
      ii. After incubation, the liquid was removed from each well by inverting the plate with gentle tapping. The plate was allowed to rest upside down for 30 seconds on the lip of a glass petri dish to aid liquid removal.
      iii. The entire plate was submerged in normal saline to rinse the wells.
      iv. Saline was removed from the wells, as in (ii) above.
      v. Steps (iii) and (iv) then were repeated a second time.
2. Test Sample Evaluation
   a. 250 µL of normal saline was added into each well in columns 1 and 12 of the plate, as well as each well of rows A and H.
   b. 250 µL of the test sample was added to the wells of rows B-G of columns 2-10.
   c. The wells of rows B-G of column 11 were kept empty.
   d. After a 5-minute contact time, the liquid was removed from each well by inverting the plate with gentle tapping. The plate was allowed to rest upside down for 30 seconds on the lip of a glass petri dish to aid liquid removal.
  e. The entire plate was submerged in normal saline to rinse the wells.
  f. Saline was removed from the wells, as in (d) above.
  g. Steps (e) and (f) then were repeated two more times.
3. Bacteria Verification Test
  a. 250 μL of 30% tryptic soy broth was added to each well after the treatment in step 2. The optical density at 595 nm was measured to obtain a T0 reading.
  b. A BreatheEasy sealing membrane was placed on the microtiter plate, and the plate was incubated at 33° C. and 60 rpm.
  c. The optical density at 595 nm was measured at hour intervals thereafter.
  d. The average absorbance for each sample was determined for each time point.

Provided below are the results of this testing: Table 6a includes actual absorbance values (at 595 nm), while Table 6b provides percentage difference from control (with positive numbers indicating improvement).

In both tables, the numbers in the leftmost column represent time in hours from the point that contact with the test solution was ceased and tryptic soy broth was added to the microtiter plate wells, i.e., the point between steps 2 and 3 of the Test Procedure reproduced above.

TABLE 6a

Regrowth of biofilms, absorbance values

| | S. aureus | | | | P. aeruginosa | | | |
|---|---|---|---|---|---|---|---|---|
| | Control | Ex. 10 | Control | Ex. 11 | Control | Ex. 10 | Control | Ex. 11 |
| 0 | 0.051 | 0.052 | 0.041 | 0.041 | 0.043 | 0.043 | 0.043 | 0.042 |
| 1 | 0.055 | 0.054 | 0.044 | 0.044 | 0.045 | 0.045 | 0.054 | 0.042 |
| 2 | 0.069 | 0.066 | 0.045 | 0.043 | 0.074 | 0.051 | 0.086 | 0.044 |
| 3 | 0.107 | 0.099 | 0.055 | 0.043 | 0.098 | 0.071 | 0.153 | 0.044 |
| 4 | 0.148 | 0.140 | 0.086 | 0.043 | 0.132 | 0.087 | 0.198 | 0.044 |
| 5 | 0.207 | 0.196 | 0.128 | 0.043 | 0.212 | 0.122 | 0.298 | 0.046 |
| 6 | 0.267 | 0.256 | 0.182 | 0.043 | 0.323 | 0.186 | 0.397 | 0.065 |
| 7 | 0.322 | 0.308 | 0.233 | 0.044 | 0.442 | 0.295 | 0.430 | 0.086 |
| 24 | 0.468 | 0.429 | 0.412 | 0.420 | 1.243 | 1.081 | 1.181 | 0.628 |

TABLE 6b

Regrowth of biofilms, percentage change from control

| | S. aureus | | P. aeruginosa | |
|---|---|---|---|---|
| | Ex. 10 | Ex. 11 | Ex. 10 | Ex. 11 |
| 0 | −2.0 | 0.0 | 0.0 | 2.3 |
| 1 | 1.8 | 0.0 | 0.0 | 22.2 |
| 2 | 4.3 | 4.4 | 31.1 | 48.8 |
| 3 | 7.5 | 21.8 | 27.6 | 71.2 |
| 4 | 5.4 | 50.0 | 34.1 | 77.8 |
| 5 | 4.3 | 66.4 | 42.5 | 84.6 |
| 6 | 3.4 | 76.4 | 42.4 | 83.6 |
| 7 | 4.3 | 81.1 | 33.3 | 80.0 |
| 24 | 8.3 | −1.9 | 13.0 | 46.8 |

The foregoing shows that inventive compositions, such as those from Examples 10 and 11, can provide superior prevention of biofilm regrowth relative to normal saline, which also happens to be the standard of care. Because safety testing (Examples 1-9) showed that both compositions are safe for use in ciliated areas, any improvement in the prevention of biofilm regrowth relative to the only previous widely used option presents a valuable tool to physicians performing procedures in or around ciliated areas, such as myringotomies.

That which is claimed is:

1. An antimicrobial composition suitable for introduction into cilia-containing areas of an animal body, said composition being free of enzymes and consisting of:
  a) a solvent component that consists of water and from 1.95 to 19.5% (w/v) ethanol, and
  b) a solute component that comprises a metal ion sequestering agent and no more than 0.2% (w/v) anionic surfactant,
  said composition having a buffered pH of from 4.8 to 5.8 and an effective solute concentration of no more than 300 mOsm/L.

2. The composition of claim 1 wherein said solute component is free of anionic surfactant.

3. The composition of claim 1 wherein said buffered pH is from 4.9 to 5.7.

4. The composition of claim 3 wherein said buffered pH is from 5.0 to 5.6.

5. The composition of claim 4 wherein said buffered pH is 5.25±0.3.

6. An antimicrobial composition suitable for introduction into cilia-containing areas of an animal body, said composition being free of enzymes and consisting of:
  a) a solvent component that consists of water and means for reducing the overall $\delta_p$ of the solvent component to a range from 14.5 to 15.9 MPa$^{1/2}$, and
  b) a solute component that comprises a metal ion sequestering agent and no more than 0.2% (w/v) anionic surfactant,
  said composition having a buffered pH of from 4.8 to 5.8 and an effective solute concentration of no more than 300 mOsm/L.

7. The composition of claim 6 wherein said means reduces the overall $\delta_p$ of the solvent component to a range of from 14.9 to 15.7 MPa$^{1/2}$.

8. The composition of claim 7 wherein said means reduces the overall $\delta_p$ of the solvent component to a range of from 14.7 to 15.8 MPa$^{1/2}$.

9. The composition of claim 8 wherein said means reduces the overall $\delta_p$ of the solvent component to 15.5±0.2 MPa$^{1/2}$.

10. The composition of claim 6 wherein said solute component is free of anionic surfactant.

11. The composition of claim 6 wherein said buffered pH is from 4.9 to 5.7.

12. The composition of claim 11 wherein said buffered pH is from 5.0 to 5.6.

13. The composition of claim 12 wherein said buffered pH is 5.25±0.3.

14. A method for treating a sinus cavity comprising introducing thereto the composition of claim 1.

15. A method for treating a middle or inner ear cavity comprising introducing thereto the composition of claim 2.

16. The method of claim 14 wherein said composition is not flushed from said cavity.

17. The method of claim 15 wherein said composition is not flushed from said cavity.

* * * * *